United States Patent [19]

Massey

[11] Patent Number: 4,685,924
[45] Date of Patent: Aug. 11, 1987

[54] PREHENSILE THUMB AND FINGER PROSTHESIS

[76] Inventor: Peyton L. Massey, 860 Gretna Green, Los Angeles, Calif. 90049

[21] Appl. No.: 784,355

[22] Filed: Oct. 4, 1985

[51] Int. Cl.[4] .............................................. A61F 2/58
[52] U.S. Cl. ........................................ 623/63; 623/64
[58] Field of Search ...................... 623/57, 64, 58–63; 128/26

[56] References Cited

U.S. PATENT DOCUMENTS

| | | | |
|---|---|---|---|
| 908,881 | 1/1909 | Nelsen | 3/12.6 X |
| 1,271,448 | 1/1918 | Dorrance | 3/12 UX |
| 1,323,671 | 12/1919 | Baehr | 3/12.8 X |
| 1,417,267 | 5/1922 | McElroy | 3/12.4 |
| 1,423,296 | 7/1922 | Armstrong | 3/12.4 |
| 1,466,163 | 8/1923 | Harris | 3/12.6 X |
| 1,499,052 | 6/1924 | Carson | 3/12 UX |
| 1,725,588 | 8/1929 | Kosek | 3/12.8 |
| 2,347,909 | 5/1944 | Jarrett | 3/12.6 X |
| 2,487,724 | 11/1949 | Pilson | 3/12 |
| 2,542,316 | 2/1951 | Farrar, Jr. | 3/12.6 X |
| 2,556,524 | 6/1951 | Drennon | 3/12.7 |
| 4,291,421 | 9/1981 | Massey et al. | 623/57 |

FOREIGN PATENT DOCUMENTS

| | | | |
|---|---|---|---|
| 412296 | 4/1925 | Fed. Rep. of Germany | 623/57 |
| 509230 | 2/1957 | Italy | 623/64 |
| 112941 | 5/1921 | United Kingdom | 623/57 |

Primary Examiner—Richard J. Apley
Assistant Examiner—James Prizant
Attorney, Agent, or Firm—William H. Maxwell

[57] ABSTRACT

A prosthesis of the hand and including a thumb and at least one finger, and other fingers as may be required, and a forearm socket, and comprised of at least said one finger articulated and biased in opposition to an adjustably fixed thumb, thereby providing a grip adapted to yield to forcible entry of an object therein and released by angular movement of the upper arm relative to the lower arm through a pull cord that operates to withdraw said finger or fingers from prehensile grasp with an object held against the thumb by said bias.

19 Claims, 7 Drawing Figures

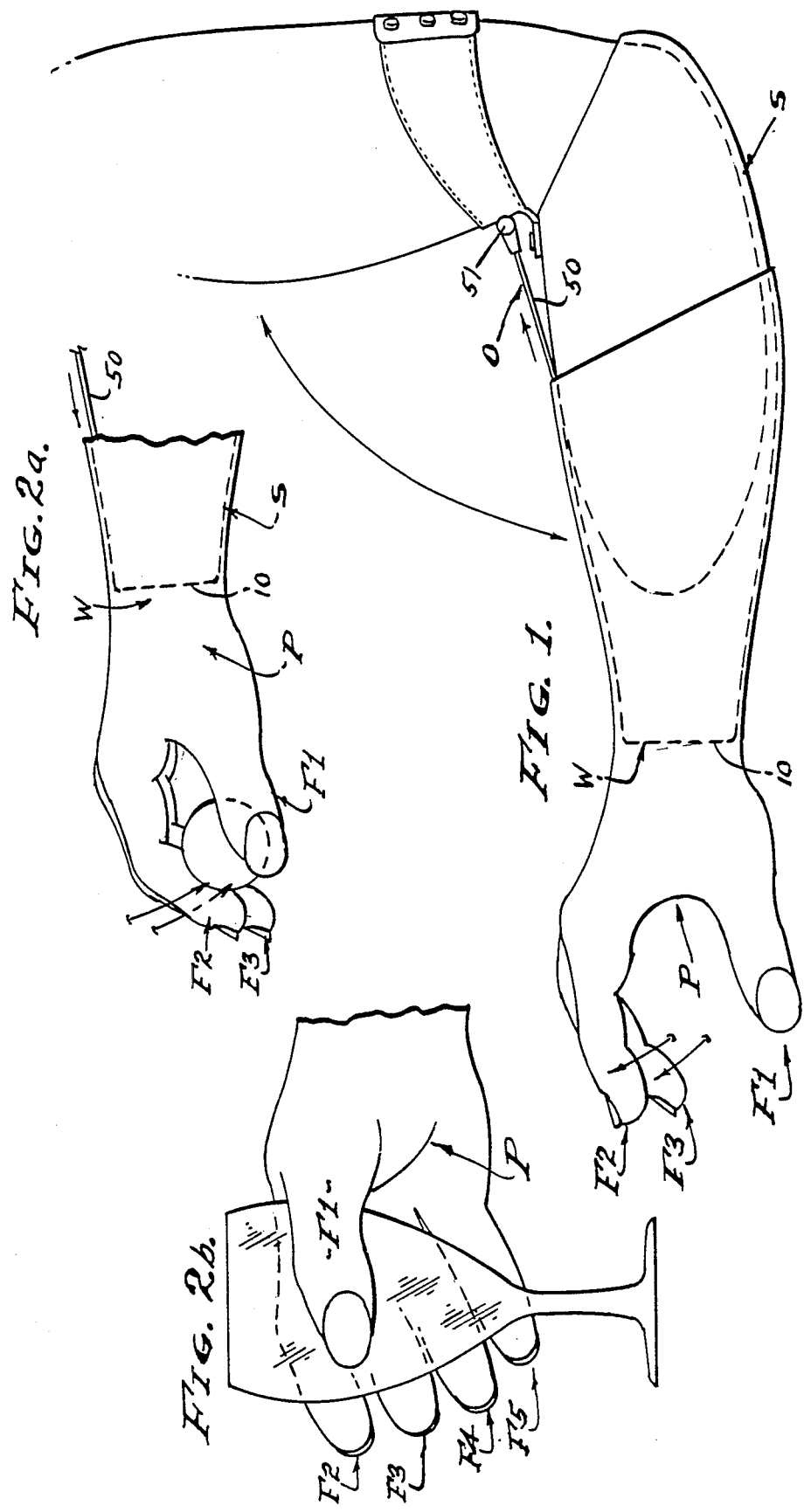

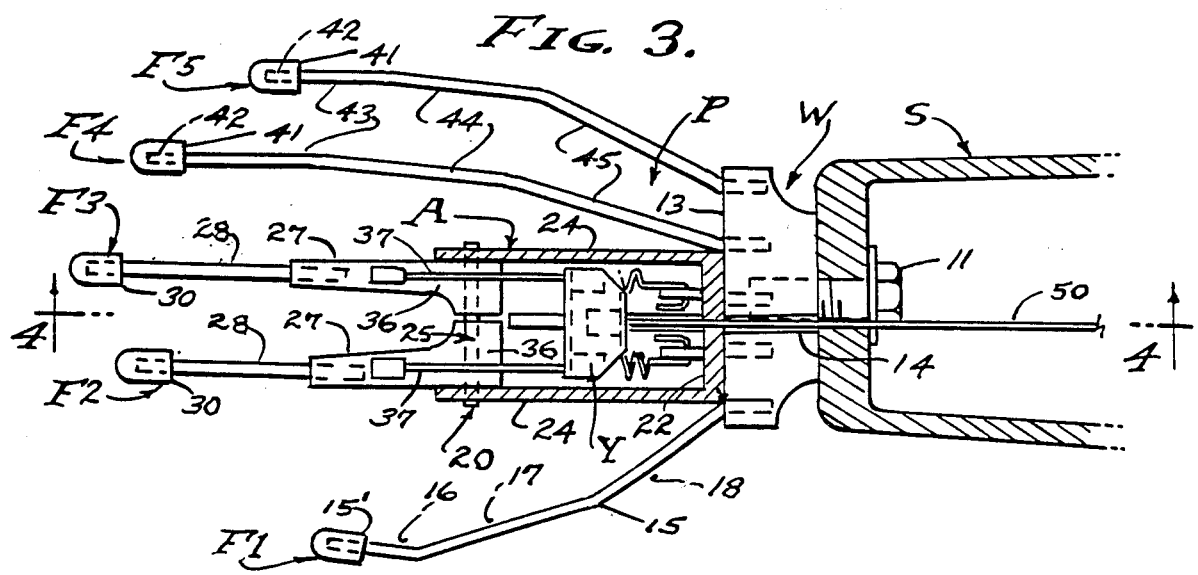
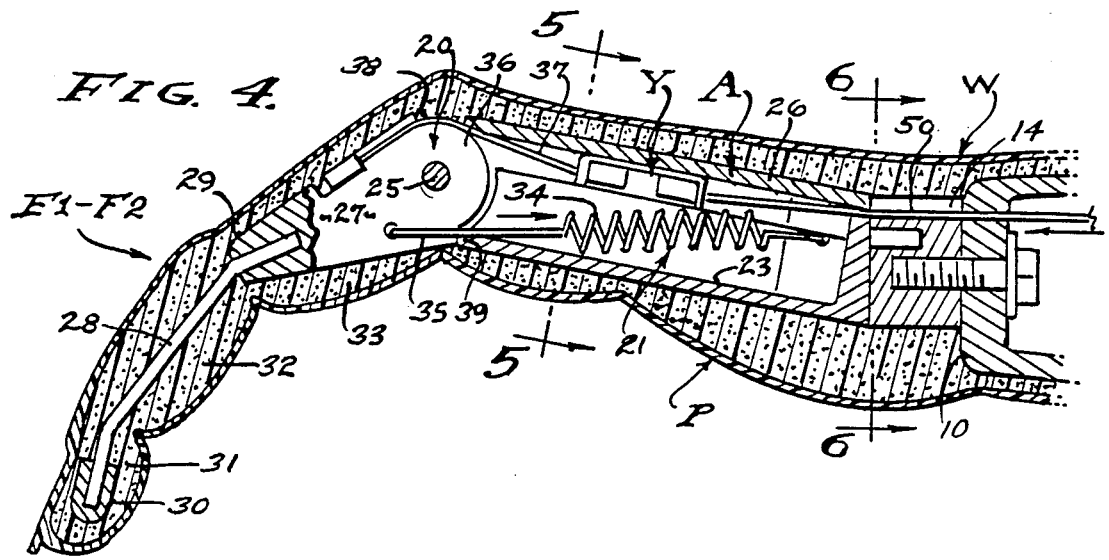
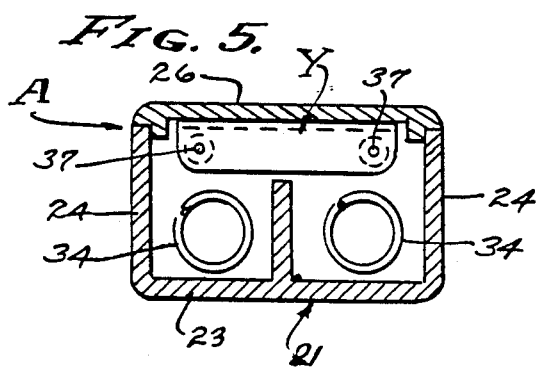
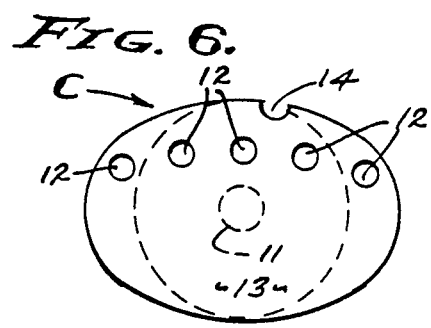

PREHENSILE THUMB AND FINGER PROSTHESIS

BACKGROUND

The prior art prostheses for the amputee of a hand or forearm are characteristically heavy cumbersome devices that are a poor substitute for a natural hand and forearm, both physically and cosmetically. It is the prehensile grip and natural appearance that has been lacking in the prior art, and though mechanical arms and hands have been devised, they have been overly engineered, complex and excessive in weight so as to be unnatural in function and in appearance. Accordingly, it is a general object of this invention to provide a prosthesis which involves the hand and forearm and provides a light weight prosthesis having a natural prehensilefunction and a natural cosmetic value as well.

The human body involves a skeletal frame that supports the flesh, the composite of which involves bone, muscle, fat, and a covering of skin, and the total of which has a certain mass and firmness associated with rigidity. In other words, the parts and limbs of the human body have certain expected physical qualities as well as mechanical functions which enable man to perform. In this case under consideration it is dexterity which is to be reastablished with the amputee, enabling him to perform substantially as before, it being an object herein to provide a "biased to grip" prosthesis that operates by forcible entry of an object therein or by deliberate mechanical release of the prehensile mode; to grip and release objects the same as a natural hand. With the present invention, there is a fixed thumb and at least one finger that moves in opposition thereto, preferably the index and/or middle finger, to establish a prehensile grip with an object therebetween. Note that there are two or three gripping members and least one of which is articulated. It is also an object of this invention to provide such a prosthesis wherein the mass is reduced, and a prosthesis wherein natural firmness is obtained, from the standpoints of comfort and appearance.

The anatomy and movement of body members involves motor means and coupling means to the simulated body members to be operated. It is the hand and its moveable index and middle fingers with which this invention is primarily concerned, it being an object herein to simulate the muscles and tendons that formerly motivated said fingers of the amputee. Accordingly, the hand is replaced mechanically as well as cosmetically, and the muscle and tendon complex is replaced by a biased grip and motor means operating the mechanical hand in a natural way. In practice, the prehensile grip is established by spring means and it is the remaining body motions and functions that are employed as the motivating power to release said grip, under mental control to be governed by the amputee. As will be decribed, It is assumed that the upper arm and a portion of the lower arm remain intact, in which case it is the relative angular displacement between the humerus and what remains of the radius and ulna that is employed to operate the prehensile movement of the at least one or more aforementioned mechanical fingers; the thumb being fixed as it is opposed to the moveable index and/or middle finger.

The prosthesis as it is disclosed herein resembles a forearm and natural hand in every respect, having an extension of the radius and ulna, having carpal and metacarpal sections, and having each of the proximal, middle and terminal phlanges of the fingers. It is an object of this invention to articulate each moveable finger (index or middle finger) as a unitary member, so that they are free to move separately and/or together in opposition to the fixed thumb. It is the proximal phalanges or long bone of each finger that is operable as a lever, and with the middle and terminal phalanges adjustably carried thereby and moved therewith. However, a natural feature of this invention is the floating articulation of a pair of fingers (index and middle finger), as may be desired; in each case the phlanges having inward and retractive movement with respect to the metacarpal section carrying the same. In practice, and as shown herein, the index and middle fingers are spring biased to close, whereby the proximal middle and terminal sections oppose an object or the thumb. It is to be understood that any one and/or all of the finger joints can be simulated as described herein.

The motor means and coupling means to the mechanical fingers provided as hereinabove referred to, simulates the tendon system of the natural arm and hand. However, the motor and coupling system herein disclosed is simplified and practical, as it employs flexible members anchored to the amputee's upper arm above the capitulum of the humerous and extended to the proximal phalanges to be moved. A feature is the coordinated movement of both the index and middle finger by yoke means, whereby the biased grip of the prothesis can be released from an object in a natural manner. Another feature is the positive action of a pull cord system, whereby the amputee can intelligently apply decreased grasping pressures as circumstances require.

It is to be understood that the anatomy to be replaced varies widely according to deformation and injury to a person's body, so that it may be any one or more of the fingers that must be replaced, it being an object herein to replace any one of the fingers as herein disclosed. Fundamentally, it is the skeletal frame, flesh and skin that is reestablished and all of which is primarly of plastic material having body thickness, softness and suppleness so as to simulate the skin and finger pads, the fingers and the palm of a real hand. Color, surface texture and imperfections (wrinkles etc.) are included along with filngernails manicured to match the person's other real hand. Accordingly. realism is achieved with the present invention, for practical as well as for psychological purposes.

An object of this invention is to provide an articulation mechanism of unit form that is adapted to occupy the interior of a hand prosthesis of natural form. That is, enlargement of the prosthesis hand is unecessary, as the articulation unit fits well within the natural hand contours; it being understood that several sizes of articulation units are to be provided, for small to large sized hands. It is also an object of this invention to provide proximal and terminal phalanges of the fixed thumb that are adjustable, and wherein each articulated finger has middle and terminal phalanges that are adjustable with respect to the proximal phalanges. It is also an object of this invention to provide for adjustment of the fourth and fifth fingers whereby each phalange thereof can be adjustably positioned for natural opposition to the usual object of be grasped. In practice, a heavy gage maleable wire or rod is used to extend from the metacarpal so as to establish the aforesaid phlanges, to be adjusted as circumstances require.

SUMMARY OF THE INVENTION

This invention relates to prostheses of the hand and a forearm and/or an upper arm socket, the prostheses having a normally closed grip so as to grasp objects inserted between the fixed thumb and at least one retractable finger. It is preferred that there be a pair of retractile fingers, though the amputee may not require this. As disclosed herein, the entire hand and a portion of the forearm is replaced, however it is to be understood that prostheses are specially fitted to the individual, so that all or part of the hand and forearm can be replaced. For example, the socket attachment can be to the upper arm, or even the shoulder. The prosthesis herein disclosed is characterized by a socket attachment to the person's body and by a hand wherein the phlanges of the thumb are adjustably fixed by the person, and wherein either or both the index and middle fingers are spring biased to oppose the fixed thumb for the insertion therebetween of an object to be grasped. It is the proximal phlange or phlanges of these fingers that are retractile by motor means, and the middle and distal phalanges adjustably fixed by the person. A feature is that the fourth and fifth fingers assist in the grasp of varied objects, and the phalanges thereof are adjustably fixed by the person, so that they oppose the object grasped. Another feature is the flesh-like softness of the entire hand prosthesis, wherein the aforesaid lever-like proximal phlanges of the articulated finger or fingers and complementary phalanges of the fixed thumb and other fingers, as well as the metacarpal palm portion of the hand are all soft and depressible. Also, there is some resilience in the wire or rod within the hand and its fingers, whereby they yield to the insertion of an object so as to comform with its contours. Release of the grip is simply by means of reducing that depression whereby an object is free to fall from or be taken from the prothesis hand. The softness is achieved by the use of foamed plastic and a skin cover of supple plastic having the general properties of skin and its texture.

The foregoing and other various objects and features of this invention will be apparent and fully understood from the following detailed description of the typical preferred form and application thereof, throughout which description reference is made to the accompanying drawings.

FIG. 1 is a side view of the prosthesis in an actuated released condition on the arm of the amputee.

FIG. 2a is a side view of the hand only shown in a biased to close grasping condition, and FIG. 2b is an anterior view of the hand only also shown in a biased to close grasping condition, with the fourth and fifth fingers assisting.

FIG. 3 is a posterior view of the hand mechanism, with the core and skin removed, and showing the articulation unit for the second and third fingers.

FIG. 4 is an enlarged sectional view taken substantially as indicated by line 4—4 on FIG. 3.

And FIGS. 5 and 6 are transverse sectional views thaken as indicated by lines 5—5 and 6—6 on FIG. 4.

PREFERRED EMBODIMENT

The present invention relates to prothetic devices that replace the missing hand, partially or completely. More particularly, this prothesis satisfies the needs of malformed and injured person's who do not have complete hands, or no hand at all. It is to be understood at the outset that malformations and injuries vary greatly, and that all or any portion of the prosthesis herein disclosed is to be employed as circumstances require. As shown, the person affected is an amputee who has lost his entire hand and portion of the arm above the styloid processes of the radius and ulna. Consequently it is the entire wrist and hand which is to be replaced and secured to the remaining portion of the radius and ulna. Accordingly, there is a socket S slideably engaged over the severed lower arm, a wrist section W simulating the carpal bones, a palm section P simulating the metacarpal bones, and fixed and articulated fingers extending from the palm section and including one or more of the following: the fixed thumb F1, the articulated index finger F2 and articulated middle finger F3, and the fixed fourth and fifth fingers F4 and F5 when so required. A feature is that all fingers are adjustable to oppose the object to be grasped, and the fingers F2 and F3 are adjustable with respect of the thumb F1 which they oppose. For the purpose of minimizing this description, the fourth and fifth fingers are shown as adjustably fixed, it being understood that they too can be motivated separately or together the same as the index and middle fingers as they are disclosed herein.

The socket S is an adapter that fits to the amputee's arm, over a secure portion thereof, in this instance over the upper part of the radius and ulna, approaching the inside head of the radius and extending over the coronoid process or elbow. The interior configuration of the socket S conforms to the flesh that surrounds that person's arm portion, and all of which is molded to fit reasonably snug therewith. For example, the socket shown receives and partially embraces the elbow so as to be captured in a working position rotatably oriented with the disposition of the upper arm and humerus thereof. Retainment of the socket and the forearm portion is ensured by the inclusion of the operating means O as hereinafter described, secured to the upper arm and providing a lever system.

The wrist section W replaces the carpal bones that normally pivot on the styloid processes of the radius and ulna, and as shown herein is fixed rigidly to the above described socket S. The socket end portion terminates at an end face 10 normal to the axis of the socket that extends to the normal length of the amputee's forearm, having a transverse cross section simulating that of a normal wrist for the particular amputee. In practice, the wrist cross section of face 10 is rounded, with variations rearward of said face to simulate the styloid process at the outside of the ulna. In other words, the socket S and its wrist section W can be fashioned to duplicate the original anatomy of the amputee. A threaded fastener 11 projects axially from the face 10 to mount the palm section P.

The palm section P replaces the metacarpal bones that normally pivot off the carpal bones, and as shown herein is positionably secured to the wrist section W at the face 10 thereof. The palm section is of substantial depth and of a length and plan configuration to duplicate that portion of the amputee's hand. For example, the length of the metacarpals of fingers F2 and F3 are substantially the same, although that of finger F3 may be slightly longer, and while the metacarpals of fingers F4 and F5 are diminishing in length. It is these natural lengths which dictate the palm configuration. In practice, the wrist cross section and palm cross section are elliptical at a coupling C that is secured to the face 10 by said fastener 11. Coupling C adapts the prosthesis hand to the face 10 of the socket S and is in the form of a receptacle that receives the articulation unit A and the finger wires or rods of the adjustably fixed thumb and fingers, as hereinafter described. Accordingly, there is a series of five finger openings 12 extending transversely of the face 13 of the coupling and into which the finger rods and plugs of the articulation unit A are inserted, in order to arrange a right or left hand prosthesis. As shown, a right hand is arranged with the thumb F1 rod inserted into the first opening 12 at the left thereof, with the pair of plugs of the articulation unit A inserted into the second and third openings to the right, and with the fourth and fifth finger F4 and F5 rods inserted respectively into the fourth and fifth openings 12 to the right. A left hand is assembled in a reverse order.

The fixed thumb finger F1 opposes one or both of the fingers F2 and F3, and as shown herein its carpal duplication is rigid in the coupling C. It is to be understood that this prosthesis is a simulation of the natural anatomy, and though the carpal and metacarpal bones of the natural thumb F1 and other fingers are at different points hinged, not so in the present invention. The fingers F2 and F3 herein are both articulated, and the thumb F1 and fingers F4 and F5 are fixed into the coupling C at either side of the articulation unit A. The thumb F1 is fixed to project from the rigid coupling C at one side of the rigid articulation unit A mounting the fingers F2 and F3, while the remaining fingers F4 and F5 are fixed to project from the rigid coupling C and the other side of said rigid unit A. A feature of the coupling C is the inclusion of a guide 14 through or over which a pull wire is trained to draw and thereby operate the articulation unit A so as to retract the fingers F2 and/or F3, and thereby to release the normal prehensile grip thereof. In practice, said guide 14 is the pull point for the actuating wire or cable that extends through the socket S and emanates therefrom at the face 10, as later described.

The thumb F1 is naturally comprised of the carpal, metacarpal, proximal and terminal phalange, all of which are hinged and muscularly controlled. However, the finger F1 herein is a maleable wire or rod 15 selectively plugged into a finger opening 12 of the coupling C as above described, and of a length inclusive of the aforesaid thumb bones and carrying a distal cap 15'. In practice, the rod 15 is bent at each natural joint, and this can be done by a technician or by the amputee himself, as may be required to establish the desired grip. The firmness of bone sections of the thumb F1 is simulated with foamed plastic or the like that occupies the interior of the skin cover that provides the cosmetic exterior, and all of which is depressible so as to adapt to the contours of the object to be grasped. In practice, the foamed plastic is sectional, there being a section 16, 17 and 18 and one simulating each bone section to be duplicated, and thereby establishing the joints therebetween. Accordingly, the thumb F1 can be readily adjusted by bending the rod 15 at the joints desired; between the carpal, metacarpal, proximal and terminal phalange.

In accordance with this invention, I provide the articulation unit A which carries the index finger F2 and middle finger F3, either of them and preferably both, and which biases them in opposition to the thumb F1, as clearly shown in the drawings. Accordingly, the articulation unit A comprises fulcrum means 20 about which these two fingers swing into retractile engagement with an object opposed by the thumb F1, and also comprising spring means 21 to bias these two fingers into yielding pressure engagement with said object. Retraction of the fingers F2 and F3 can be by simple withdrawal of said object, in which case the spring means yields to release the object, and alternate, retraction of the fingers is by operating means O which comprises a pull member from an anchor means on the amputee's body, and extending to one or both of the fingers as the case may be, to retract them at the will of the amputee. In practice, the fingers F2 and F3 are self leveling and operate in unison, as next described.

The articulation unit A is a framework of box configuration occupying the metacarpal portion of the prothesis hand, the palm portion P of the hand, and it is located in the area of the second and third metacarpals and is in alignment with the second and third finger openings 12 in the coupling C. As shown, the unit A is comprised of a box structure having a back wall 22 with a pair of plugs received in the spaced openings 12, a bottom 23 and spaced means 21. The side walls 24 carry the fulcrum means 20 side walls 24 with a partition therebetween to establish a pair of chambers to house the spring in the form of a transverse pivot 25 on which the fingers F2 and F3 independently swing side by side. A cover 26 encloses the workings of the unit A, which also includes a yoke Y to which the individual fingers F2 and F3 are coupled and from which a pull member in the form of a cord or cable 50 extends to an anchor means for actuation.

Fingers F2 and F3 are alike so that a description of one will suffice for the other. As shown each finger is naturally comprised of the proximal phalange or long bone, the middle phalange, and the terminal phalange, and all of which are hinged and muscularly controlled. However, the fingers F2 and F3 herein are a combination lever 27 and a maleable wire or rod 28 extension carried side by side on the pivot 25. The levers 27 simulate the long bone phalanges, the rods 28 being plugged into the joint end 29 of the levers 27, and of lengths inclusive of the aforesaid middle phalanges and distal phalanges and each carrying a distal cap 30. In practice, the rod 28 is bent at each natural joint, and this can be done by a technician or by the amputee himself, as may be required to establish the desired grip. The firmness of bone sections of the fingers F1 and F2 are simulated with foamed plastic or the like that occupies the interior of the skin covers that provide the comsmetic exteriors, and all of which are depressible so as to adapt to the contours of the object to be grasped. In practice, the foamed plastic is sectional, there being a section 31, 32 and 33 and one simulating each bone section to be duplicated, and thereby establishing the joints therebetween. Accordingly, the fingers F2 and F3 can be readily adjusted by bending the rods 28 at the joints desired; between the proximal phalanges, the middle phalanges, and the terminal phalanges.

In accordance with this invention, the fingers F2 and F3 are biased to close and to thereby grip in a prehensile manner, in response to spring means 21, simulating the natural tendon function that closes the human grip. Accordingy, the spring means 21, in each instance, is comprised of a tension spring 34 housed in a chamber of the articulation unit A, anchored at the back wall 22 and having a live end 35 trained over the anterior or periphery of a hub 36 that turns free on the pivot 25. The live end 35 of spring 34 is pinned or otherwise hooked to the hub 36 at a lever radius so as to produce a closing force or moment. Alternately, the fingers F2 and F3 are deliberately retractile through the operating means so as to open the aforementioned prehensile grip, in response to the will of the amputee, simulating the natural tendon functions that opens the human grip. Accordingly, the operating means is comprised, in each instance, of a wire or cable 37 (50) trained over the posterior or top periphery of the hub 36. The live end of the cable 37 is secured to the hub 36 at a lever radius so as to produce an opening force or moment. A feature of this invention is the equalizing effect between the two fingers F2 and F3 that are retracted in unison, the pull cables 37 being extended to the opposite sides of the yoke Y that slides freely in the unit A and which is drawn from its center by the pull member or cable 50.

In accordance with this invention there is the operating means O which comprises the pull cable 50 from an anchor means 51 at the upper arm (humerus), and extending to and through the pull point 14 and connected to the center of yoke Y. The pair of pull cables 37 are branches of cable 50, connections thereof being made by swage fittings or the like. In practice, the cables are small diameter wire, cable 50 being trained to extend along the inside of the arm socket S. to emanate through the guide 14 between the openings 12 that receive the two plugs of the articulation unit A. The opening and closing of the finger F2 and F3 is controlled by stop shoulders 38 and 39 on the finger hubs 36, that engage posterior (back) and anterior (palm) lips of the cover 26 and bottom 23 of the articulation unit A. The front of the articulation box structure is open and from which the two levers 27 of fingers F2 and F3 emanate.

Fingers F4 and F5 are alike so that a description of one will suffice for the other. As shown each finger is naturally comprised of the proximal phalange or long bone, the middle phalange, and the terminal phalange, and all of which are hinged and muscularly controlled. However, like the thumb F1, the fingers F4 and F5 herein are a maleable wire or rod 40 selectively plugged into a finger opening 12 of the coupling C as hereinabove described, and of a length inclusive of the metacarpal, the proximal phalange or long bone, the middle phalange, and the distal or terminal phalange, and each carrying a distal cap 41. In practice, the rod 40 is bent at each natural joint, and this can be done by a technician or by the amputee himself, as may be required to establish the desired grip. The firmness of bone sections of the fingers F4 and F5 are simulated with foamed plastic or the like that occupies the interior of the skin covers that provide the cosmetic exteriors, and all of which are depressible so as to adapt to the contours of the object to be grasped. In practice, the foamed plastic is sectional, there being a section 42, 43, 44 and 45 and one simulating each bone section to be duplicated, and thereby establishing the joints therebetween. Accordingly, the fingers F4 and F5 can be readily adjusted by bending the rods 40 at the joints desired; between the carpal, metacarpal, proximal phalange, middle phalange, and distal or terminal phalange in each instance.

From the foregoing it will be apparent that the skeletal framework and duplication of the anatomy simulates the real and natural bones and their normal artiulation. A characteristic feature is the normal closed bias of the prothesis hand ready for the insertion or reception of an object in a prehensile manner, as it is adjusted to grip the same. The grip function is established by a firm spring pressure that imposes the prehensile force between the thumb F1 and the opposing index and middle fingers F2 and F3. The fingers F4 and F5 assist in the grip as may be desired, by adjusting them to engage the object to be handled. For Example, the fingers F4 and F5 can be turned inward at the metacarpal region so as to enhance the ability to cup the object with the palm of the prosthesis. In practice, the fleshy simulation of the prosethesis is in the foamed plastic core thereof that fills the interior with a depressible solid comprised of areas and/or sections which simulate the articulated sections of the natural human hand. For example, the core is notched, or separated partially or completely, so as to establish weakened fold points that simulate natural joints that separate the aforesaid sections between which the rods 14, 28 and 40 are bent as circumstances require. A feature is the guidance of the cables 37 and 50 in grooves so that they are captured in working position trained over the hubs 36 at a maximum radius beneath the skin covering. It is to be understood that the skin cover D is a soft and supple simulation of a person's skin, sculpted and tinted for realism.

Having described only a typical preferred form and application of my invention, I do not wish to be limited or restricted to the specific details herein set forth, but wish to reserve to myself any modifications or variations that may appear to those skilled in the art as set forth within the limits of the following claims.

I claim:

1. A prosthesis for replacing the human hand for attachment to a forearm socket; including;

a coupling member replacing the carpal portion of the hand and attached to the socket and having a transverse series of openings, means in the form of an articulation unit carried by the coupling member and replacing the metacarpal portion of the hand and comprising at least one finger thereof and having a spring means biasing the at least one finger to a closed grip in yielding opposition to a thumb finger, the transverse series of openings in the coupling member receiving the fixed fingers and at least one plug of the articulation unit for selective positioning and attachment of said finger and said articulation unit in the formation of right and left hand protsheses, and the thumb finger and remaining fingers of the prosthesis at either side of the articulation unit and its at least one finger being fixedly carried by the coupling member.

2. The hand prosthesis as set forth in claim 1, wherein the coupling member is rotatably adjustable on the socket and attached thereto by a centered fastener.

3. The hand prosthesis as set forth in claim 1, wherein the articulation unit replaces the metacarpal portion of the hand and comprises at least the second index finger thereof.

4. The hand prosthesis as set forth in claim 1, wherein the articuation unit replaces the metacarpal portion of the hand and comprises at least the third finger thereof.

5. The hand prosthesis as set forth in claim 1, wherein the articulation unit replaces the metacarpal portion of the hand and comprises the second index finger and third finger thereof.

6. The hand prothesis as set forth in claim 1, wherein the proximal phalange of the at least one finger of the articulation unit is a lever operated by the spring means to bias said closed grip.

7. The hand prosthesis as set forth in claim 1, wherein the proximal phalange of the at least one finger of the articulation unit is a lever operated by the spring means to bias said closed grip, and wherein the middle and terminal phalange of the at least one finger of the articulation unit are comprised of a maleable rod for adjusting said closed grip by bending the same.

8. The hand prosthesis as set forth in claim 1, wherein the metacarpal, proximal phalange and terminal phalange of the fixed thumb finger are comprised of a maleable rod for adjusting said closed grip by bending the same.

9. The hand prosthesis as set forth in claim 1, wherein the metacarpal, proximal phalange, middle phalange and terminal phalange of the fixed remaining fingers other than the fixed thumb are comprised of a maleable rod for adjustment assisting said closed grip by bending the same.

10. The hand prosthesis as set forth in claim 1, wherein the proximal phalange of the at least one finger of the articulation unit is a lever operated by the spring means to bias said closed grip, wherein the middle and terminal phalange of the at least one finger of the articulation unit are comprised of a makeable rod for adjusting said closed grip by bending the same, and wherein the metacarpal, proximal phalange and terminal phalange of the fixed thumb finger are comprised of a maeable rod for adjusting said closed grip by bending the same.

11. The hand prosthesis as set forth in claim 1, wherein the proximal phalange of the at least one finger of the articulation unit is a lever operated by the spring means to bias said closed grip, wherein the middle and terminal phalanges of the at least one finger of the articulation unit are comprised of a maleable rod for adjusting said closed grip by bending the same, wherein the metacarpal, proximal phalange and terminal phalange of the fixed thumb, finger are comprised of a maleable rod for adjusting said closed grip by bending the same, and wherein the metacarpal, proximal phalange, middle phalange and terminal phalange of the fixed remaining fingers are comprised of a maleable rod for adjustment assisting said closed grip by bending the same.

12. A prosthesis for replacing the human hand partially and entirely for attachment to a forearm socket and the like, and including;
 a coupling member replacing the carpal portion of the hand and attached to the socket and having a transverse series of openings,
 means in the form of an articulation unit carried by the coupling member and replacing the metacarpal portion of the hand and comprising at least one finger thereof and having a spring means biasing the at least one finger to a closed grip in yielding opposition to a thumb finger, and having operating means to remove said bias and release said grip at the will of a person wearing the prothesis,
 the transverse series of openings in the coupling member receiving the fixed fingers and at least one plug of the articulation unit for selective positioning and attachment of said finger and said articulation unit in the formation of right and left hand protheses,
 and the thumb finger and remaining fingers of the prosthesis at either side of the articulation unit and its at least one finger being fixedly carried by the coupling member.

13. The hand prosthesis as set forth in claim 12, wherein the operating means is comprised of a lever replacing the proximal phalange of the finger to be operated to release said grip.

14. The hand prosthesis as set forth in claim 12, wherein the operating means is comprised of a lever replacing the proximal phalange of the finger to be operated to release said grip, and a pull member extending therefrom to an anchor point on a relatively moveable portion of the person's body above a portion to which the socket is attached.

15. The hand prosthesis as set forth in claim 1, wherein a core of depressible material encapsulates the metacarpal, proximal phalange, middle phalange and terminal phalange portions of the proshesis hand and its fingers, so as to depress to the contours of an object grasped and thereby increase holding ability of the prosthesis.

16. The hand prosthesis as set forth in claim 15, wherein a cosmetic skin covers said core and is supple so as to enable the core to depress.

17. The hand prothesis as set forth in claim 1, wherein the fingers of the prosthesis include deflective rods so as to yield to the configuration of an object grasped and thereby increase the holding ability of the prosthesis.

18. The hand prosthesis as set forth in claim 15, wherein the fingers of the prosthesis include deflective rods so as to yield to the configuration of an object grasped and thereby increase the holding ability of the prothesis.

19. The hand prosthesis as set forth in claim 18, wherein a cosmetic skin covers said core and is supple so as to enable the core to depress.

* * * * *